(12) United States Patent
Levy et al.

(10) Patent No.: US 8,962,603 B2
(45) Date of Patent: *Feb. 24, 2015

(54) METHOD FOR POST COITAL CONTRACEPTION IN OVERWEIGHT OR OBESE FEMALE SUBJECTS USING ULIPRISTAL ACETATE

(75) Inventors: Delphine Levy, Paris (FR); Andre Ulmann, Paris (FR); Henri Camille Mathe, Paris (FR); Erin Gainer, Paris (FR)

(73) Assignee: Laboratoire HRA-Pharma, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/575,086

(22) PCT Filed: Dec. 1, 2010

(86) PCT No.: PCT/EP2010/068646
§ 371 (c)(1),
(2), (4) Date: Oct. 12, 2012

(87) PCT Pub. No.: WO2011/091890
PCT Pub. Date: Aug. 4, 2011

(65) Prior Publication Data
US 2013/0210788 A1 Aug. 15, 2013

Related U.S. Application Data

(60) Provisional application No. 61/300,393, filed on Feb. 1, 2010.

(51) Int. Cl.
*A61K 31/57* (2006.01)

(52) U.S. Cl.
CPC ..................... *A61K 31/57* (2013.01)
USPC ...................................... 514/177

(58) Field of Classification Search
None
See application file for complete search history.

(56) References Cited

PUBLICATIONS

Faculty of Sexual & Reproductive Healthcare New Product Review (Ulipristal acetate (EllaOne), Oct. 2009 at www.fsrg.org.*
Glasier et al. Ulipristal Acetate versus levonorgestrel for emergency contraception: a randomised non-inferiority trial and meta-analysis, Jan. 29, 2010, Lancet 2010, vol. 375, pp. 555-562.*
Creinin et al. Progesterone Receptor Modulator for Emergency Contraception: A Randomized Controlled Trial, Obstet Gynecol. 2006, vol. 108, pp-1089-1097.*
Reel et al. Antiovulator and Postcoital Antifertility Activity of the Antiprogestin CDB-2914 When Administered as Single, Multiple, or Continous Doses to Rats. Contraception (1998), vol. 58, pp. 129-136.*
Stratton et al. A single mid-follicular dose of CDB-2914, a new antiprogestin, inhibits folliculogenesis and endometrial differentiation in normally cycling women. Human Reproduction (2000), vol. 15, pp. 1092-1099.*
Edelman et al. Impact of obesity on oral contraceptive pharmacokinetics and hypothalamic-pituitary-ovarian activity. Contraception (2009) vol. 80, pp. 119-127.*
International Search Report and Written Opinion for International PCT/EP2010/068646 Issued by the International Searching Authority on Feb. 2, 2011.
Anonymous: "New Product Review—Ulipristal Acetate (ella0NE)" Internet Citation, [Online] Oct. 2009, pp. 1-5, Faculty of Sexual & Reproductive Healthcare; Retrieved from the Internet: URL:http://www.ffprhc.org.uk/admin/uploads/el-laOneNewProductReview1009.pdf> [retrieved on Jan. 20, 2011] whole document especially p. 3, chapter "How effective is ulipristal?".
Anonymous: "Ulipristal Acetate (ella0NE)—APC/DTC Briefing Document" [Online] Sep. 2009, London New Drugs Group; Retrieved from the Internet: URL:http://www.nelm.nhs.uk/upload/Ulipristal__Sept2009.pdf> [retrieved on Jan. 20, 2011] whole document especially p. 11-12, chapter "Meta-analysis".
Glasier, Anna F., et al.: "Ulipristal acetate versus levonorgestrel for emergency contraception: a randomised non-inferiority trial and meta-analysis" Lancet (North American Edition), vol. 375, No. 9714, Jan. 29, 2010, pp. 555-562; whole document especially p. 557, Table 1; p. 559, left hand column, 1. 40-46.
Anonymous: "Ulipristal Acetate, Background Document for Meeting of Advisory Committee for Reproductive Health Drugs" [Online] Jun. 17, 2010, FDA, Division of Reproductive and Urologic Products, Office of New Drugs, Center for Drug Evaluation and Research; Retrieved from the Internet: URL:http://www.fda.gov/downloads/AdvisoryCommittees/CommitteesMeetingMaterials/Drugs/ReproductiveHealthDrugsAdvisoryCommittee/UCM215425.pdf> [retrieved on Jan. 20, 2011] whole document especially p. 37-38, chapter 4.3.1.
ellaONE Ulipristal—European Medicines Agency—European Public Assessment Report from the Internet: URL:http://www.ema.europa.eutema/index.jsp?curl=pges/medicines/human/medicines/00__21-01-2011 p. 1 of 1.
Attardi et al., "In vitro antiprogestational/antiglucocorticoid activity and progestin and glucocorticoid receptor binding of the putative metabolites and synthetic derivatives of CDB-2914, CDB-4124, and mifepristone," J. Steroid Biochem Molec. Bio., 2004, 88; pp. 277-288.
Orihuela, P., "Drug evaluation: Ulipristal, a progesterone receptor antagonist as a contraceptive and for the treatment of uterine fibroids," Current Opinion in Investigational Drugs, 2007, vol. 8, No. 10; pp. 859-866.

(Continued)

*Primary Examiner* — Melenie McCormick
*Assistant Examiner* — Taina D Matos Negron
(74) *Attorney, Agent, or Firm* — Ascenda Law Group PC

(57) ABSTRACT

The invention provides a method for providing post coital contraception in a female subject, comprising providing the subject with a therapeutically effective amount of ulipristal acetate, wherein the female subject is overweight or obese.

6 Claims, 1 Drawing Sheet

(56) References Cited

PUBLICATIONS

Erin E. Gainer et al, "Pharmacologic properties of CDB(VA)-2914", Steroids 60 (2003) 1005-1011, Elsevier Inc.

Diana L. Blithe et al., "Development of the selective progesterone receptor modulator CDB-2914 for clinical indications", Steroids 68 (2003) 1013-1017, Elsevier Inc.

Passaro et al., "Luteal phase dose-response relationships of the antiprogestin CDB-2914 in normally cycling women", Human Reproduction (2003) 18:1820-1827.

HRA Pharma Press Release: HRA Pharma commences US Phase III trial of second-generation emergency contraceptive; Dec. 7, 2006.

HRA Pharma Press Release: HRA Pharma commences UK-based Phase III trial of Ella, a second generation emergency contraceptive; Mar. 26, 2007.

Furedi, "New Emergency contraceptive method ellIaOne—is it worth the price?" Reproductive Health Matters 2009:17(34):187-188.

Cameron et al. "Ulipristal acetate compared to levonorgestrel for emergency contraception within five days of unprotected intercourse: a randomised controlled trial", Abstract 8th Congress of the European Society of Gynecology; Roma Sep. 10-13, 2009.

Fine et al. "A multicenter trial of ulipristal acetate for late-intake emergency contraception", Abstract 8th Congress of the European Society of Gynecology; Roma Sep. 10-13, 2009.

"CHMP Assessment Report for EellaONE"—European Medicines Agency, Evaluation of Medicines for Human Use, EMEA/261787/2009.

Crenin et al. "Progesterone receptor modulator for emergency contraception" American College of Obstetricians and Gynecologists vol. 108, No. 5, Nov. 2006.

Communication pursuant to Rule 114(2) EPC (observations by a third party) as filed in the European Patent Office in EP Application No. 10717084.7 on Jul. 25, 2014.

Communication pursuant to Rule 114(2) EPC (observations by a third party) as filed in the European Patent Office in EP Application No. 10717084.7 on Sep. 4, 2014.

* cited by examiner

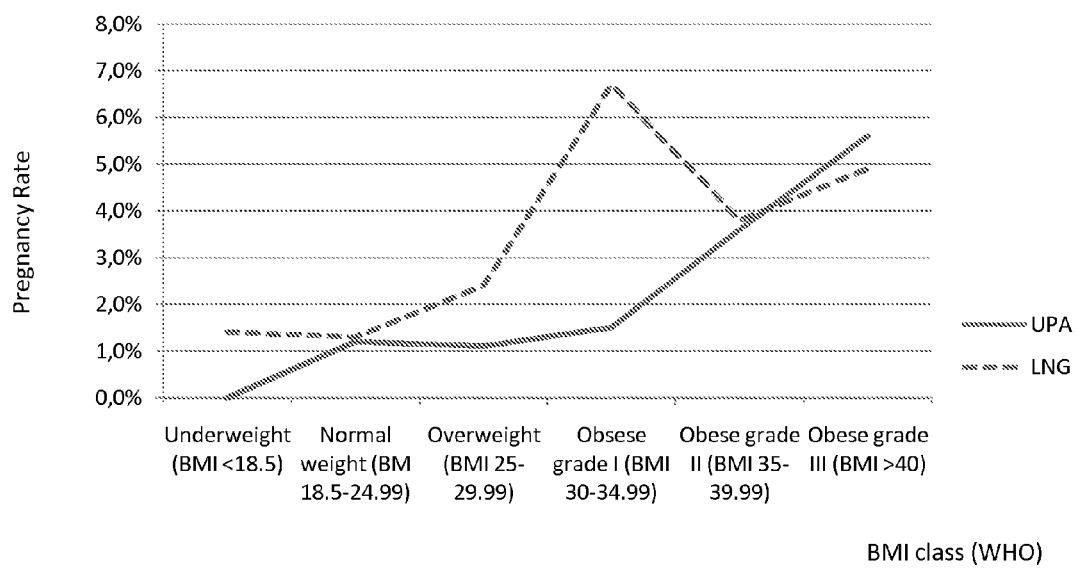

METHOD FOR POST COITAL CONTRACEPTION IN OVERWEIGHT OR OBESE FEMALE SUBJECTS USING ULIPRISTAL ACETATE

The present invention relates to a method for providing post coital contraception in a female subject who is overweight or obese.

BACKGROUND TO THE INVENTION

Emergency contraception (EC), i.e. contraceptive indicated for the prevention of pregnancy following unprotected intercourse or a known or suspected contraceptive failure, is a woman's second chance for primary prevention of pregnancy.

For decades, various high-dose estrogen-progestin regimens have been prescribed by experienced gynecologists for EC, generally involving the off-label administration of high doses of combined oral contraceptive pills. It is only in the mid-nineteen-nineties that dedicated products appeared, following requests from regulatory agencies and women's groups for properly labelled and packaged preparations. Initially, dedicated products consisted of high-dose estrogen-progestin preparations. In 1999, based on WHO publications of randomized clinical trials demonstrating that 0.75 mg levonorgestrel twice was as effective as combined estrogen-progestin preparations, HRA Pharma's NorLevo® became the first progestin-only EC to be granted a marketing authorization in Western countries. Since that time, several preparations have been approved elsewhere in the world (e.g. Plan B®, Levonelle®, Postinor®), and currently the standard of care for EC within 72 hours of unprotected intercourse is the administration of 1.5 mg of levonorgestrel, either in a single dose or in two 0.75 mg doses taken 12-24 hours apart. A number of countries have granted non-prescription status to these preparations based on levonorgestrel's well-characterized safety profile and limited contraindications.

Although EC with 1.5 mg of levonorgestrel has undoubtedly contributed to the prevention of unwanted pregnancies, it has its limitations in terms of efficacy: its efficacy rate drops significantly with the time elapsed since unprotected intercourse. Reported pregnancy rates from WHO trials rise from approximately 1.5 to 2.6%, respectively, for intake 0 to 24 hrs as compared to intake 48-72 hrs after intercourse. In addition, for a woman who presents for EC more than 72 h after intercourse, the only available method with a proven efficacy is the insertion of a copper intra-uterine device (although not approved or labelled for such use in the United States), although use is limited by both availability and the need for insertion by a skilled health-care professional.

Obesity appears to significantly affect the therapeutic efficacy of oral contraceptives. For example, Holt et al. 2005 showed that being overweight increased the risk of becoming pregnant. Edelman et al. (2009) found that compared with woman having a normal body mass index, obese women had altered pharmacokinetics including half-life, clearance and time to reach steady state of the oral contraceptive. Obesity is an epidemic problem in many countries and especially within the United States. http://www.contraceptivetechnology.org/Trussell ContraceptionforObeseWomen.ppt—retrieved Dec. 13, 2009). Accordingly, there is a growing need to develop effective means of emergency contraception for obese women.

Ulipristal acetate (also referred to as CDB-2914, VA2914, HRP-2000 and RTI 3021-012) is an orally-active selective progesterone receptor modulator (SPRM) that has been developed for emergency contraception (EC). Ulipristal acetate inhibits or delays ovulation in a dose-dependent fashion (Stratton et al, 2000). In a double-blind non-inferiority trial, ulipristal acetate was shown to be as efficacious as levonorgestrel for preventing pregnancy when used within 72 hours of UPI (Creinin et al, 2006). Ulipristal acetate has been approved in Europe, under trademark EllaOne®, for use as an emergency contraceptive.

SUMMARY OF THE INVENTION

The inventors have now found out that the body mass index (BMI), used to classify obesity status of a subject, has an impact on efficacy of ulipristal acetate and levonorgestrel as emergency contraceptives. However the efficacy of contraception decreases significantly less with ulipristal acetate than with levonorgestrel.

The invention thus provides a method for providing post coital contraception in a female subject, comprising providing the subject with a therapeutically effective amount of ulipristal acetate, wherein the female subject is overweight or obese.

Preferably the female subject has a body mass index (BMI) above about 25, in particular between about 25 and about 35, e.g. between about 25 and about 30. In an embodiment, the female subject has a body mass index (BMI) above about 30, e.g. between about 30 and about 35.

Especially, for women overweight or with grade I obesity (BMI between about 25 and about 35), the risk of pregnancy is divided by 3 when taking ulipristal acetate versus levonorgestrel.

LEGEND TO THE FIGURE

The FIGURE is a graph that shows efficacy of ulipristal acetate (UPA) vs. levonorgestrel (LNG) as emergency contraception, according to BMI class (WHO).

DETAILED DESCRIPTION OF THE INVENTION

Obesity is defined as a condition of abnormal or excessive accumulation of adipose tissue, to the extent that health may be impaired. The body mass index (BMI; $kg/m^2$) provides the most useful, albeit crude, population-level measure of obesity. Obesity has also been defined using the WHO classification of the BMI classes for adults: underweight (<18.5), normal weight (18.5 to 24.99), overweight (25 to 29.99), obese grade I (30 to 34.99), obese grade II (35 to 39.99), obese grade III and more (≥40). See WHO, Global database on Body Mass Index, http://apps.who.int/index.jsp?introPage=intor_3/html.

The effect of BMI in pooled phase III studies was assessed by comparing pregnancy rates among sub-groups of the study populations according to WHO weight classes. Pregnancy rates increased starting from BMI>25, and for women with a BMI>30, the 95% CI of the observed pregnancy rate overlapped with the expected pregnancy rate. A meta-analysis of two comparative studies showed that efficacy of ulipristal acetate remained constant for underweight and normal (BMI below 25) and for overweight and obese grade I (BMI 25-34.99) subjects, whereas it decreased in obese grade II (BMI 35 and above) subjects. Still, ulipristal acetate was significantly more effective than levonorgestrel in women with a BMI>25.

Ulipristal acetate, formerly known as CDB-2914, designates within the context of this application 17α-acetoxy-11β-[4-N,N-dimethylamino-phenyl]-19-norpregna-4,9-diene-3,20-dione, represented by formula I:

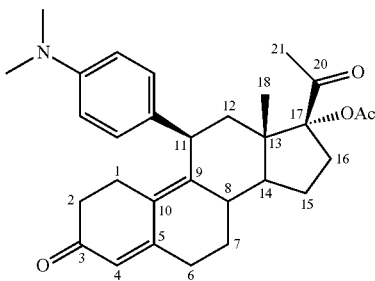

Ulipristal acetate, and methods for its preparation, are described e.g., in U.S. Pat. Nos. 4,954,490; 5,073,548, and 5,929,262, as well as in international patent applications WO2004/065405 and WO2004/078709, incorporated herein by reference.

Its main metabolite is monodemethylated CDB-2914 (CDB-3877A), that is 17α-acetoxy-11β-[4-N-methylaminophenyl)-19-norpregna-4,9-diene-3,20-dione.

The subject, who may be also designated by the term "patient", may be any woman in need of a post coital contraception, preferably of an emergency contraception.

Any woman of reproductive age may need post coital contraception or emergency contraception at some point to avoid an unintended pregnancy. It is meant to be used in situations of unprotected intercourse, such as:
when no contraceptive has been used;
when there is a contraceptive failure or incorrect use, including:
  condom breakage, slippage, or incorrect use;
  non-compliance with dosage regimen for combined oral contraceptive pills;
  non-compliance with dosage regimen for progestogen-only pill (minipill);
  more than two weeks late for a progestogen-only contraceptive injection (depot-medroxyprogesterone acetate or norethisterone enanthate);
  more than seven days late for a combined estrogen-plus-progestogen monthly injection;
  dislodgment, delay in placing, or early removal of a contraceptive hormonal skin patch or ring;
  dislodgment, breakage, tearing, or early removal of a diaphragm or cervical cap;
  failed coitus interruptus (e.g., ejaculation in vagina or on external genitalia);
  failure of a spermicide tablet or film to melt before intercourse;
  miscalculation of the periodic abstinence method or failure to abstain on fertile day of cycle;
  IUD expulsion; or in cases of sexual assault when the woman was not protected by an effective contraceptive method.

Preferably post coital contraception is provided within 120 hours, preferably within 72 hours, after unprotected intercourse. For instance, post coital contraception may be provided more than about 2, 3, 4 and up to 5 or even 6 days after unprotected intercourse. Preferably, post coital contraception is provided within about 75, 80, 90, or 96 hours after unprotected intercourse. Post coital contraception may be provided up to 120 hours, preferably about 100, 110, 120 hours after unprotected intercourse.

In the present invention post coital contraception most preferably is an emergency contraception.

Ulipristal acetate may be administered by any convenient route, including oral, buccal, parenteral, transdermal, vaginal, uterine, rectal, etc.

For a brief review of present methods for drug delivery, see, Langer, Science 249:1527-1533 (1990), which is incorporated herein by reference. Methods for preparing administrable compounds are known or are apparent to those skilled in the art and are described in more detail in, for example, Remington's Pharmaceutical Science, 17th ed., Mack Publishing Company, Easton, Pa. (1985), which is incorporated herein by reference, and which is hereinafter referred to as "Remington."

For solid compositions, conventional nontoxic solid carriers may be used which include, for example, pharmaceutical grades of mannitol, lactose, starch, magnesium stearate, sodium saccharine, talcum, cellulose, glucose, sucrose, magnesium, carbonate, and the like. For oral administration, a pharmaceutically acceptable nontoxic composition is formed by incorporating any of the normally employed excipients, such as those carriers previously listed.

Oral solid dosage forms preferentially are compressed tablets or capsules. Compressed tablets may contain any of the excipients described above which are diluents to increase the bulk of the ulipristal so that production of a compressed tablet of practical size is possible. Binders, which are agents which impart cohesive qualities to powdered materials are also necessary. Starch, gelatin, sugars such as lactose or dextrose, and natural and synthetic gums are used. Disintegrants are necessary in the tablets to facilitate break-up of the tablet. Disintegrants include starches, clays, celluloses, algins, gums and crosslinked polymers. Lastly small amounts of materials known as lubricants and glidants are included in the tablets to prevent adhesion to the tablet material to surfaces in the manufacturing process and to improve the flow characteristics of the powder material during manufacture. Colloidal silicon dioxide is most commonly used as a glidant and compounds such as talc or stearic acids are most commonly used as lubricants. Procedures for the production and manufacture of compressed tablets are well known by those skilled in the art (See Remington).

Capsules are solid dosage forms using preferentially either a hard or soft gelatin shell as a container for the mixture of ulipristal or a metabolite thereof and inert ingredients. Procedures for production and manufacture of hard gelatin and soft elastic capsules are well known in the art (See Remington).

Buccal forms or devices are also useful, such as those described in U.S. patent application 20050208129, herein incorporated by reference. U.S. patent application 20050208129 describes a prolonged release bioadhesive mucosal therapeutic system containing at least one active principle, with an active principle dissolution test of more than 70% over 8 hours and to a method for its preparation. Said bioadhesive therapeutic system comprises quantities of natural proteins representing at least 50% by weight of active principle and at least 20% by weight of said tablet, between 10% and 20% of a hydrophilic polymer, and compression excipients, and comprising between 4% and 10% of an alkali metal alkylsulphate to reinforce the local availability of active principle and between 0.1% and 1% of a monohydrate sugar.

For parenteral administration, fluid unit dosage forms are prepared utilizing the compounds and a sterile vehicle, water being preferred. Ulipristal acetate, depending on the vehicle and concentration used, can be either suspended or dissolved in the vehicle. In preparing solutions the compound can be dissolved in water for injection and filtered sterilized before filling into a suitable vial or ampoule and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions can be prepared in substantially the same manner except that the compounds are suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of ulipristal acetate.

Additionally, a suppository can be employed to deliver ulipristal acetate. The active compound can be incorporated into any of the known suppository bases by methods known in the art. Examples of such bases include cocoa butter, polyethylene glycols (carbowaxes), polyethylene sorbitan monostearate, and mixtures of these with other compatible materials to modify the melting point or dissolution rate. These suppositories can weigh from about 1 to 2.5 g.

Transdermal delivery systems comprising a penetration enhancer and an occlusive backing are of use to deliver ulipristal acetate. Examples of penetration enhancers include dimethyl sulfoxide, dimethyl acetamide and dimethylformamide.

Systems comprising polymeric devices which slowly release or slowly erode and release within the body to provide continuous supplies of ulipristal acetate are also of use. Suitable delivery systems include subcutaneous devices or implants such as those routinely used to deliver norgestrienone or progestin R2323 and other medicaments.

Ulipristal acetate is preferably in form of an oral dosage, such as a tablet or a capsule, preferably a tablet.

In a preferred embodiment, it is provided as pharmaceutical tablet for oral administration, comprising ulipristal acetate in an amount of 3 to 18 wt %, together with the following excipients: a diluent in an amount of 60 to 95 wt %, a binding agent in an amount of 1 to 10 wt %, croscarmellose sodium in an amount of 1 to 10 wt %, and magnesium stearate in an amount of 0 to 5 wt %.

According to preferred embodiments, the composition, preferably in form of a tablet, comprises 10% wt ulipristal acetate and is designed to contain from 5 to 50 mg ulipristal acetate, preferably 10, 20, or 30 mg.

The diluent may be selected from any pharmaceutically acceptable agent or combination of agents that increases the bulk quantity of ulipristal acetate so that production of a compressed tablet of practical size is possible. In a preferred embodiment, the diluent is selected from the group consisting of a monosaccharide, a disaccharide, a derivative polyol of a monosaccharide and hydrates thereof. The term 'derivative polyol of a monosaccharide' stands for a sugar alcohol such as mannitol, xylitol or sorbitol. Preferably the diluent is selected from the group consisting of lactose monohydrate and mannitol. In a most preferred embodiment, the diluent is lactose monohydrate is an amount of 65 to 92 wt %, more preferably 70-85 wt %.

The binding agent, or binder, may be selected from any pharmaceutically acceptable agent (or combination of agents) which imparts cohesive qualities to powdered materials. The binding agent may be selected from starch, gelatin, sugars such as cellulose derivatives, and natural and synthetic gums may be used. Advantageously, the binding agent of the tablet is selected from the group consisting of polymers. The binding agent may be a natural polymer material such as polysaccharide, or a synthetic polymer such as a plastic polymer. Preferably, the binding agent is hydroxypropyl methyl cellulose and/or povidone. In a preferred embodiment, the binding agent is or comprises povidone, preferably 1.5% to 8.5 wt % of povidone, even more preferably between 3-7 wt %, most preferably about 5 wt % povidone.

The tablets preferably comprise croscarmellose sodium. Croscarmellose sodium is a disintegrant, e.g., facilitates break-up of the tablet. Croscarmellose sodium may be used alone or in combination with other disintegrants, preferably alone. It is preferably present in an amount of 1 to 10 wt %, preferably 1.5 to 8.5 wt %, and more preferably 4.5 to 5.5 wt %, or even more preferably about 5 wt %.

In preferred embodiments, the tablets of the present invention contain magnesium stearate. While magnesium stearate may be used in combination with other lubricants, it is preferably used alone, in an amount comprised between 0.5 and 5 wt %.

Preferably, the tablet according to the present invention comprises lactose monohydrate as a diluent and povidone as a binding agent.

In a more specific embodiment, the tablet comprises: ulipristal acetate 5 to 15 wt %, lactose monohydrate 71 to 87 wt %, povidone 4.5 to 5.5 wt %, croscarmellose sodium 4.5 to 5.5 wt % and magnesium stearate 1 to 4 wt %, where the total percentage adds up to 100.

In an even more specific embodiment, the tablet comprises: ulipristal acetate 10%, lactose monohydrate 79 wt %, povidone 5 wt %, croscarmellose sodium 5 wt % and magnesium stearate 1 wt %.

Tablets may be prepared according to techniques known per se in the art. Suitable methods include direct compression ("dry blending"), dry granulation followed by compression, and wet granulation followed by drying and compression. Several methods include the use of compacting roller technology such as a chilsonator or drop roller, or molding, casting, or extrusion technologies. The tablet can be a coated tablet or an uncoated tablet.

In the preparation of the tablets, commercial mixtures comprising diluents and binding agents may be used, such as Avicel® (microcrystalline cellulose), Starlac® (lactose monohydrate 85% with maize starch 15%) or, Ludipress® (lactose monohydrate 93% with Povidone 7%).

In a particular embodiment, a 30 mg ulipristal acetate tablet may be manufactured as follows. Lactose monohydrate 79 wt %, ulipristal acetate 10 wt % and povidone 5 wt % are mixed and purified water is added. This granulation step is followed by a drying step in an oven at 40° C. Croscarmellose sodium 5 wt % and magnesium stearate 1 wt % are added for the lubrication step. The obtained formulation is compressed to get the tablet, which shows the following formulation (Table 1).

TABLE 1

30 mg ulipristate acetate tablet:

| Ingredients | Quantity for one tablet (mg) | Quantity for one tablet (wt %) |
|---|---|---|
| Ulipristal acetate | 30.00 | 10 |
| Lactose Monohydrate | 237.00 | 79 |
| Povidone | 15.00 | 5 |
| Croscarmellose sodium | 15.00 | 5 |
| Magnesium stearate | 3.00 | 1 |
| Total | 300.00 | 100 |

Further ulipristal acetate tablets are provided hereafter.

TABLE 2

Other ulipristal acetate tablet formulations:

| Ingredients | 10 mg tablet Quantity for one tablet in mg (wt %) | 30 mg tablet Quantity for one tablet in mg (wt %) |
| --- | --- | --- |
| Ulipristal acetate | 10.00 (10) | 30.00 (10) |
| Lactose Monohydrate | 79.00 (79) | 246.00 (82) |
| Povidone | 5.00 (5) | 9.00 (3) |
| Croscarmellose sodium | 5.00 (5) | 12.00 (4) |
| Magnesium stearate | 1.00 (1) | 3.00 (1) |
| Total | 100.00 (100) | 300.00 (100) |

The subject may provided with a kit comprising i) a dosage form, preferably an oral dosage form such as a tablet, comprising ulipristal acetate and ii) a printed matter stating that ulipristal acetate is more efficient than levonorgestrel in providing post coital contraception when the subject is overweight or obese, compared to a non-overweight or non-obese subject.

Preferably the dosage form comprises 30 mg ulipristal acetate.

Such printed matter serves as a labelling for the medicament. For instance it is conveniently a leaflet inserted into the packaging of the medicament, or it may be the packaging itself, on which the information is printed.

The FIGURE and example illustrate the invention without limiting its scope.

EXAMPLE

Example 1

Effect of BMI on Pregnancy Rates 1.1. Phase II Protocol

This Phase II, prospective, multicenter, randomized, double-blind study was performed to compare the efficacy of a single 50 mg dose of ulipristal acetate (unmicronized in gelatine capsule) with two 0.75 mg doses of levonorgestrel used as an emergency postcoital contraceptive within 72 hours of unprotected intercourse. The study was carried out in seven sites in seven different states in the United States.

Women (aged ≥18 years old) not using hormonal contraception and who requested emergency contraception within 72 hours (3 days) after unprotected coitus defined by lack of contraceptive use, condom breakage or other barrier contraceptive method failure were included. Subjects were required to have a history of regular menstrual cycles (mean length of 24-42 days with intra-individual variation of ±5 days). At least one normal menstrual cycle (two menses) was required after delivery, abortion, or discontinuation of hormonal contraception. Subjects were excluded from the study if they were pregnant at screening or enrollment (assessed by a high-sensitivity urine pregnancy test), pregnant or breastfeeding within the 2 months before screening, using an intra-uterine device (IUD) or female or male sterilization as a contraceptive method, uncertain about the date of the last menstrual period (±3 days), had been nauseated or vomited in the 2 weeks before screening, had used oral glucocorticoid replacement therapy in the year before the screening, or were currently enrolled in any other investigational trial.

Each woman returned for a follow-up visit 5 to 7 days after the expected onset of her next menstrual period and a high-sensitivity urine pregnancy test was performed. The primary objective was to compare the efficacy, as determined by pregnancy prevention, of 50 mg ulipristal acetate and levonorgestrel used as an emergency postcoital contraceptive within 72 hours of unprotected intercourse.

As defined in the protocol, the primary analysis was performed on the modified intent-to-treat (mITT) population, which included all subjects randomized, who had received at least one dose of the study treatment and had a post-treatment pregnancy evaluation.

1.2. Phase III Protocol

This was a prospective, single-blind (subject and sponsor blind, investigator not blind), randomized, multicenter, 2-arm parallel comparative study designed to evaluate the efficacy, safety and tolerability of a single dose of ulipristal acetate (30 mg) compared to levonorgestrel (1.5 mg) administered for EC within 120 hours after unprotected intercourse. It was performed in 10 centers in Europe and 25 centers in the US.

Women (aged ≥16 years), with regular menstrual cycles (between 24 and 35 days and intra-individual variations less than or equal to 5 days), who presented for EC within 120 hours after unprotected intercourse at a participating study site and who met the inclusion/exclusion criteria were enrolled into the study after they signed informed consent form. Subjects were excluded from the study in case of ongoing pregnancy or breast-feeding or current use of hormonal contraception or IUD.

The study medication (ulipristal acetate 30 mg or levonorgestrel 1.5 mg) was administered according to a random allocation procedure generated electronically. Treatment was administered orally immediately after all eligibility criteria (including negative urine pregnancy test) had been verified. At the first follow-up visit (5-7 days after expected onset of menses), a subject was determined to be not pregnant if she had a negative urine pregnancy test and menses had occurred, or was determined to be pregnant if she had a positive pregnancy test confirmed by serum β-hCG; the subject was then considered pregnant and the second follow-up (12-14 days after onset of expected menses) visit was omitted. If at the second follow-up visit, a subject still had a negative urine pregnancy test but menses had not occurred, a serum β-hCG test was performed.

The primary objective of the study was to provide evidence that the pregnancy rate observed after taking ulipristal acetate (30 mg) within 72 hours of unprotected intercourse is lower than the expected pregnancy rate in the absence of EC.

The efficacy analysis was performed on the modified Intent To Treat (mITT) population which included all subjects who had received study drug, were participating in the study for the first time (multiple enrollments were allowed in the protocol), had a known pregnancy status after emergency contraception intake, were aged up to and including 35 years, and did not have a pregnancy identified as having started before ulipristal acetate intake or not compatible with study drug failure, based on independent evaluation.

In order to ensure unbiased evaluation of pregnancy data, an independent, autonomous DSMB composed of two experts in the field of gynecology, one methodologist and one expert in ethical questions was established to review incidence of pregnancy with respect to unacceptability threshold and give recommendations during the course of the clinical trial. In addition, the DSMB assessed whether each pregnancy was "compatible" or "not compatible" with treatment failure based on available data.

1.3. Meta-Analysis

The effect of BMI was assessed by comparing pregnancy rates among sub-groups of the study populations according to common BMI categories. Pregnancy rates increased starting from BMI>25, and for women with a BMI>30 the 95% CI of the observed pregnancy rate overlapped with the expected pregnancy rate. However, the differences between different BMI classes did not reach statistical significance.

In the logistic regression model used to compare ulipristal acetate and levonorgestrel in the meta-analysis, BMI was found to be a significant predicting factor of pregnancy, regardless of the treatment group (p<0.0001). When the efficacy of ulipristal acetate and levonorgestrel are then compared following stratification of the population according to World Health Organization BMI classes: underweight (<18.5), normal weight (18.5 to 24.99), overweight (25 to 29.99), obese grade I (30 to 34.99), obese grade II (35 to 39.99), obese grade III and more (≥40), differential efficacy is observed. Results are presented in Table 3.

TABLE 3

Pregnancy rate by WHO BMI class (ulipristal acetate and levonorgestrel)

| BMI class (WHO) | N | Pregnancy rate Ulipristal acetate | Levonorgestrel |
|---|---|---|---|
| Underweight | 145 | 0 | 1.43% |
| Normal weight | 2087 | 1.16% | 1.33% |
| Overweight | 744 | 1.06% | 2.45% |
| Obese grade I | 285 | 1.47% | 6.71% |
| Obese grade II | 107 | 3.64% | 3.85% |
| Obese grade III | 77 | 5.56% | 4.88% |

BMI classes were grouped: underweight+normal weight, overweight and obese grade I and obese grade II and III. Pregnancy rates in these pooled BMI classes are displayed below (Table 4), and are shown on the FIGURE.

TABLE 4

Pregnancy rate by grouped BMI class (ulipristal acetate and levonorgestrel)

| BMI Class (WHO) | N | Pregnancy Rate Ulipristal acetate | Levonorgestrel | Odds Ratio [95% CI] | p-value |
|---|---|---|---|---|---|
| Underweight & Normal | 2232 | 1.08% | 1.34% | 0.81 [0.37; 1.73] | NS |
| Overweight & Obese I | 1029 | 1.17% | 3.68% | 0.31 [0.11; 4.44] | p = 0.0073 |

TABLE 4-continued

Pregnancy rate by grouped BMI class (ulipristal acetate and levonorgestrel)

| BMI Class (WHO) | N | Pregnancy Rate Ulipristal acetate | Levonorgestrel | Odds Ratio [95% CI] | p-value |
|---|---|---|---|---|---|
| Obese II and more | 184 | 4.40% | 4.30% | 0.74] 1.02 [0.23; 4.44] | NS |

For women overweight or with grade I obesity (BMI [25-34.99]), the risk of pregnancy is divided by 3 when taking ulipristal acetate versus levonorgestrel and this is highly statistically significant (p=0.0073).

REFERENCES

Creinin M D, Schlaff W, Archer D F, Wan L, Frezieres R, Thomas M, Rosenberg M, Higgins. Progesterone Receptor Modulator for Emergency Contraception: A Randomized Controlled Trial. Obstetrics & Gynecology 2006; Vol. 108; No. 5: 1089-97;
Edelman et al. Contraception 80:119-127 (2009);
Holt et al. Obstetrics and Gynecology, 105:46-52 (2005);
Wilcox A J, Weinberg C R, Baird D D. Timing of Sexual Intercourse in Relation to Ovulation. NEJM 1995; Vol. 33: 1518-21

The invention claimed is:

1. A method for providing post coital contraception in a woman comprising administering to the woman an amount of about 30 mg of ulipristal acetate within about 120 hours after intercourse, wherein the woman is overweight, having a BMI of 25 to 29.99, or obese grade I, having a BMI of 30-34.99.

2. The method of claim 1, wherein post coital contraception is provided within about 72 hours after unprotected intercourse.

3. The method of claim 1, wherein post coital contraception is provided from about 72 hours to about 120 hours after unprotected intercourse.

4. The method of claim 1, wherein the post coital contraception is emergency contraception.

5. The method of claim 1, wherein the ulipristal acetate is administered in an oral dosage form.

6. The method of claim 5, wherein the oral dosage form is a tablet.

* * * * *